United States Patent
Ide et al.

(10) Patent No.: US 6,797,169 B1
(45) Date of Patent: Sep. 28, 2004

(54) FILTER MEMBRANES FOR PHYSIOLOGICALLY ACTIVE SUBSTANCES

(75) Inventors: Shoichi Ide, Miyazaki (JP); Toshiaki Noda, Miyazaki (JP)

(73) Assignee: Asahi Kasei Pharma Corporation, Tokyo (JP)

( * ) Notice: Subject to any disclaimer, the term of this patent is extended or adjusted under 35 U.S.C. 154(b) by 20 days.

(21) Appl. No.: 10/048,550

(22) PCT Filed: Aug. 18, 2000

(86) PCT No.: PCT/JP00/05548

§ 371 (c)(1),
(2), (4) Date: May 1, 2002

(87) PCT Pub. No.: WO01/14047

PCT Pub. Date: Mar. 1, 2001

(30) Foreign Application Priority Data

Aug. 20, 1999 (JP) .......................................... 11/234727

(51) Int. Cl.[7] ............................................. B01D 71/06
(52) U.S. Cl. ........................... 210/500.27; 210/500.45; 210/500.41; 210/500.29; 210/500.23
(58) Field of Search ................................ 210/651, 650, 210/500.29, 500.41, 645, 500.23, 500.27; 436/538, 536

(56) References Cited

U.S. PATENT DOCUMENTS

| | | | |
|---|---|---|---|
| RE3,277 E | * | 1/1869 | Tuyere ......................... 56/208 |
| 4,609,464 A | * | 9/1986 | Aoyagi et al. ......... 210/321.79 |
| 5,698,281 A | * | 12/1997 | Bellantoni et al. ......... 428/35.7 |
| 6,391,657 B1 | * | 5/2002 | Bernhardt et al. .......... 436/538 |
| 6,517,843 B1 | * | 2/2003 | Ellis et al. ................ 424/204.1 |

OTHER PUBLICATIONS

Noriyoshi et al.; "Protein–Containing Composition and its Production"; Patent Abstracts of Japan, of JP 09–301886, Nov. 25, 1997.
Naoki et al.; "Virus Removing Method"; Patent Abstracts of Japan, of JP 10–337445, Dec. 12, 1998.
Shoichi et al.; "Production of Cuprammonium Regenerated Cellulose Porous Hollow Fiber Membrane"; Patent Abstracts of Japan, of JP 04–371221, Dec. 24, 1992.

* cited by examiner

Primary Examiner—Ana Fortuna
(74) Attorney, Agent, or Firm—Finnegan, Henderson, Farabow, Garrett & Dunner, L.L.P.

(57) ABSTRACT

Filter membranes for efficiently eliminating pathogens such as viruses from solutions of drugs or physiologically active substances employed as starting materials thereof which are contaminated with pathogens such as viruses. These filter membranes, which can simultaneously achieve favorable performance of eliminating small viruses and a high physiologically active substance-permeability, can be obtained by controlling the membrane characteristics to give a ratio (BP/$\gamma$) of the bubble point BP (MPa) to the surface tension $\gamma$ (N/m) of 110 or above, and/or logarithmic elimination ratios of swine parvovirus at 0 to 5 l/m$^2$ filtration volume and at 50 to 55 l/m$^2$, and regulating the permeability for bovine immunoglubulin, wherein the monomer content amounts to at least 80%, to 70% or more. These filter membranes make it possible to provide drugs or starting materials therefor with little fear of the contamination with viruses, etc. and, therefore, are useful in the fields of pharmacy, medicine and the like.

7 Claims, No Drawings

FILTER MEMBRANES FOR PHYSIOLOGICALLY ACTIVE SUBSTANCES

TECHNICAL FIELD

The present invention relates to a filter membrane used to effectively remove pathogens such as viruses from solutions of medicinal products or physiologically active products used as the raw materials thereof.

BACKGROUND ART

In the purification process of plasma derivatives or biopharmaceutical products, technology for preventing virus infection, which may be caused by administration of products, has been used. A method of inactivating or removing viruses is employed as this type of technology. As examples of the method of inactivating viruses, a heat treatment method and a chemical treatment method (Solvent/Detergent (S/D) treatment, for example) can be given. As examples of the method of removing viruses, a membrane filtration method can be given. In the membrane filtration method, particles are separated by size exclusion based on a sieving principle. Therefore, viruses can be removed only by size irrespective of chemical or thermal characteristics thereof. Because of this, the membrane filtration method using a virus removal membrane has been widely put into practical use on an industrial scale.

The heat treatment method exerts little effect on heat-resistant human parvovirus B19, hepatitis A virus, and the like. The S/D treatment method has essentially no effect on human parvovirus B19, poliovirus, reovirus, and SV-40 having no lipid envelope. In particular, since human parvovirus B19 is heat resistant and has no lipid envelope, the virus removal membrane is effective for inactivating or removing human parvovirus B19.

In the purification process of plasma derivatives or biopharmaceutical products, it is necessary to increase removability or inactivation capability of viruses and permeability for physiologically active products at the same time.

Virus removal membranes available at present are either a membrane which allows high-molecular-weight physiologically active products such as human immunoglobulin and Factor VIII to pass therethrough, but exhibits inferior small virus removal performance, or a membrane which can remove small viruses, but cannot allow high-molecular-weight physiologically active products such as human immunoglobulin or Factor VIII to pass therethrough at a practical level.

Specifically, conventional virus removal membranes are either a membrane which allows high-molecular-weight physiologically active products such as human immunoglobulin or Factor VIII to pass therethrough, but cannot remove small viruses such as human parvovirus B19, or a membrane which can remove small viruses such as human parvovirus B19, but cannot allow high-molecular-weight physiologically active products such as human immunoglobulin or Factor VIII to pass therethrough at a practical level.

Japanese Patent Application Laid-open No. 7-265674 discloses a polyvinylidene fluoride membrane capable of effectively removing small particles from liquid and exhibiting minimum adsorption, for which an integrity test before actual use can be employed. Although the inventors clam that this membrane is useful for removing viruses from a solution, its capability of allowing high-molecular-weight physiologically active products to pass therethrough with high permeability is still unconcern.

Japanese Patent No. 1873816 and U.S. Pat. No. 4,808,315 disclose polymer porous hollow fiber membranes. These hollow fiber membranes have a specific micropore structure effective for removing viruses from a solution of physiologically active products. These hollow fiber membranes are characterized by the specific micropore structure exhibiting superior virus removability and high permeability for physiologically active products at the same time. However, these patents neither describe nor suggest whether or not the membranes are effective in the case of sieving high-molecular-weight physiologically active products such as human immunoglobulin or Factor VIII from small viruses such as human parvovirus B19 or poliovirus.

Japanese Patent Application Laid-open No. 4-505579 discloses a membrane for separating viruses from a solution. This membrane is a composite asymmetric membrane which selectively separates viruses from a solution which includes viruses. This membrane exhibits ≧3 log reduction value for bacteriophage Φ×174 (28 nm) and ≧3 log reduction value for small viruses such as human parvovirus B19 or poliovirus. However, the membrane exhibits an extremely low human immunoglobulin permeability of 10–20% and, therefore, cannot be used in practice.

Conventional filter membranes which selectively separate physiologically active products from small viruses such as human parvovirus B19 have a problem whereby virus removability decreases as the volume of filtration is increased during continuous filtration. In particular, filter membranes excelling in initial virus removability have a problem whereby virus removability suddenly decreases accompanied by an increase in the volume of filtration.

DISCLOSURE OF THE INVENTION

The present invention has been achieved to solve the above problems in the prior art. Specifically, an object of the present invention is to provide a filter membrane for solutions of medicinal products or physiologically active products used as the raw materials of medicinal products which may be contaminated with viruses, which can allow the physiologically active products to pass therethrough at a practical level and remove small viruses such as human parvovirus B19 or poliovirus, of which the characteristics can be maintained without substantial change depending on the volume of filtration. As a result, another object of the present invention is to provide technology for providing safer products.

The present inventors have conducted extensive studies in order to achieve the above object to attain the present invention.

Specifically, according to one aspect, the present invention provides a filter membrane for solutions of physiologically active products, of which the ratio (BP/γ) of a bubble point BP (MPa) to surface tension γ (N/m) is 110 or more and permeability for bovine immunoglobulin with a monomer content of 80% or more is 70% or more.

According to another aspect, the present invention provides a filter membrane for solutions of physiologically active products, of which the log reduction value for porcine parvovirus are 3 or more at both 0–5 $l/m^2$ filtration and 50–55 $l/m^2$ filtration, and permeability for bovine immunoglobulin with a monomer content of 80% or more is 70% or more.

According to still another aspect, the present invention provides a filter membrane for solutions of physiologically active products, of which the BP/γ ratio is 110 or more, the log reduction value for porcine parvovirus are 3 or more at both 0–5 l/m² filtration and 50–55 l/m² filtration, and permeability for bovine immunoglobulin with a monomer content of 80% or more is 70% or more. In the pore structure of the filter membrane, the thickness of a region with a pore size logarithmic standard deviation $\sigma_g$ of 2.0 or less is preferably 3–90 μm. The purified water permeation rate of the filter membrane is preferably 70–200 l/h/0.1 MPa per m² of the membrane area. The filter membrane preferably has no skin layer on the surface. The thickness of the filter membrane is preferably 5–100 μm.

The pore size characteristics of the membrane of the present invention may be represented by the BP/γ ratio and/or the log reduction value for porcine parvovirus, and permeability for bovine immunoglobulin with a monomer content of 80% or more.

The BP/γ ratio and the log reduction value for porcine parvovirus are indexes regarding to the pore structure of the filter membrane. The BP/γ ratio relates to the pore structure at early stage of filtration. The log reduction value for porcine parvovirus is an index relating not only to performance at early stage of filtration, but also to the durability of filtration performance over time.

The virus concentration in the filtrate may vary depending on the volume of filtration. In the case of a membrane having a small capacity for capturing viruses, the log reduction value for porcine parvovirus decreases as the volume of filtration is increased. A membrane exhibiting no or only a small decrease in the log reduction value for porcine parvovirus has a large capacity for capturing viruses. The capacity for capturing viruses increases as the volume of the region with a certain degree homogeneity in the pore structure of the membrane is increased. This causes the membrane to have excellent durability of the log reduction value for porcine parvovirus over time. In the present invention, the log reduction value for porcine parvovirus of 3 or more at both 0–5 l/m² filtration and 50–55 l/m² filtration are indexes indicating the degree of durability, pore structure, capacity for capturing viruses, and homogeneity of the membrane. An interfacial destruction phenomenon is used to specify the pore structure of the filter membrane. A bubble point test is used as a convenient method for determining the maximum pore size of the membrane. This method has been used by Bechold et al. (H. Bechold et al., Kolloid Z., 55, 172 (1931), JIS K3832).

In this method, the membrane is wetted using liquid with a surface tension of γ (N/m). When pressure is gradually applied to the membrane using gas, continuous bubbling occurs at the surface of the membrane under a specific gas pressure. This gas pressure is called the bubble point BP (MPa).

Any conventional measuring methods determine the pressure under which occurrence of continuous bubbling is confirmed, by naked eye observation, as the bubble point. However, in the case where the area of the membrane is small, occurrence of bubbles may be overlooked since the amount of bubbling is small. Moreover, separation of bubbles which have attached to the surface of the membrane before applying pressure (which are not produced by interfacial destruction phenomenon) may be mistaken for the separation of bubbles produced by the interfacial destruction phenomenon. Therefore, errors tend to occur in those methods.

In the present invention, the pressure (MPa) under which continuous bubbling quantitatively occurs in an amount of 3.0 ml/min per cm² is defined as the bubble point BP in order to reduce measurement errors.

The present inventors have found a correlation between the BP/γ ratio and the removal of human parvovirus B19. In more detail, the present inventors have found that a membrane having pore size characteristics with a BP/γ of 110 or more can remove human parvovirus B19 efficiently.

A method of analyzing particle removal performance is used to indirectly specify the pore structure of the filter membrane. The removal performance is generally expressed by using the reduction value of model particles having the average particle size which is close to the average pore size of the membrane and a particle size distribution as narrow as possible.

In the technical field within the present invention, specific viruses or phages are used as particles having the above characteristics. Porcine parvovirus has an average particle size of 20–25 nm, has an extremely narrow particle size distribution in a non-aggregated state, and has no risk of infection to human. Therefore, porcine parvovirus is a suitable model particle in the field to be applied the present invention.

In the present invention, the reduction value of human infectious small viruses such as human parvovirus B19 may be estimated based on the BP/γ ratio. Moreover, in the present invention, the reduction value of human infectious small viruses such as human parvovirus B19 may also be estimated from the reduction value for porcine parvovirus which has similar particle size and other characteristics to those of human parvovirus B19.

The reduction value for porcine parvovirus is expressed by the log reduction value (LRV) and can be calculated using the following equation.

$$LRV = \log_{10}(N_0/N_f)$$

$N_0$: the number of porcine parvovirus in the feed solution
$N_f$: the number of porcine parvovirus in filtrate In the present invention, the log reduction value for porcine parvovirus must be 3 or more at both 0–5 l/m² filtration and 50–55 l/m² filtration.

The virus filtration is performed under the condition of a pressure of 0.0785 MPa and a temperature of 25° C. by constant pressure dead-end filtration. The virus concentration in the filtrate may vary depending on the volume of filtration. In the present invention, $\geq 3$ LRV for porcine parvovirus means that both LRV of the filtrate at 0–5 l/m² filtration and LRV of the filtrate at 50–55 l/m² filtration are 3 or more.

A membrane of which the LRV decreases as the volume of filtration is increased has a small capacity for capturing viruses. A membrane of which the LRV does not decrease, or decreases to only a small extent has a large capacity for capturing viruses. Therefore, the LRVs at the two points can indicate the membrane structure characteristics.

It is difficult to produce a membrane which can allow solution of physiologically active products to pass therethrough at a practical level, and excels in LRV durability in the removal of small viruses such as human parvovirus B19 or poliovirus using a conventional technique.

The membrane of the present invention excels in LRV durability even in the removal of small viruses due to increased capacity of the region with a certain degree of homogeneity in the pore structure of the membrane. As the feed solution for determining the log reduction value for porcine parvovirus, a culture supernatant obtained after culturing ESK cells (pig kidney cells) infected with porcine parvovirus in Dulbecco's MEM medium containing 3% fetal bovine serum was used.

The concentration of porcine parvovirus in the solution before filtration and in the filtrate was determined by a $TCID_{50}$ method utilizing agglutination of chicken erythrocyte after culturing each solution added to the ESK cells for 10 days, respectively.

There is no established general technique (assay) for measuring the concentration of human parvovirus B19 by observation of cell degeneration or the like. Concentration measurement (assay) using a PCR method may be used in some cases. However, it is difficult to obtain precise data on the virus reduction value due to insufficient sensitivity. Therefore, effectiveness of the method of removing or inactivating human parvovirus B19 is estimated by evaluation using porcine parvovirus or canine parvovirus, for which high sensitivity assay by the observation of cell degeneration are established. Actually, a technique, which is determined effective for inactivating or removing human parvovirus B19 by evaluation using porcine parvovirus or canine parvovirus, exhibits practical performance in the process for producing products.

In the membrane filtration of physiologically active products, a decrease in permeability means an increase in the degree of clogging the pore structure of the membrane by the physiologically active products. Clogging the pore structure of the membrane causes an increase in the loss of physiologically active products captured in the membrane, a decrease in the concentration of physiologically active products in the filtrate, a decrease in the filtration volume per unit area of the membrane, and the like, thereby increasing costs in the process for producing products. Therefore, the practical level of permeability for physiologically active products during membrane filtration step in the industrial process for producing products is 70% or more, and preferably 80% or more.

Permeability for physiologically active products varies depending on types of substances and properties of the solution. Human immunoglobulin has a molecular weight of 160,000–900,000, which is generally the greatest range for physiologically active products put into practical use in the fields of medicine and medication. Moreover, human immunoglobulin has a high aggregation property to a great extent. Therefore, it seems to be difficult to improve permeability for human immunoglobulin.

In the process for producing plasma derivatives using human blood as the raw material, human blood is usually subjected to a plurality of purification processes such as Cohn fractionation, in which protein components of blood plasma are fractionated by utilizing the difference in affinity with ethanol, and chromatography. The resulting human immunoglobulin is subjected to virus removal using a filter membrane.

The content of contaminants or polymers in human immunoglobulin before filtration is smaller than that in bovine immunoglobulin. Therefore, a membrane exhibiting high permeability for bovine immunoglobulin is easily estimated to exhibit the same or higher permeability for human immunoglobulin. The membrane of the present invention, of which the permeability for bovine immunoglobulin with a monomer content of 80% or more is 70% or more, brings significant effects during filtration of medicinal products or physiologically active products used as the raw materials of medicinal products from the viewpoint of costs in the process for producing products.

Permeability for bovine immunoglobulin was calculated as follows.

$$\text{Permeability for bovine immunoglobulin} = C_f/C_0 \times 100$$

$C_f$: Bovine immunoglobulin concentration before filtration (feed solution)

$C_0$: Bovine immunoglobulin concentration after filtration (filtrate)

Filtration for calculating the permeability for bovine immunoglobulin is performed under a pressure of 0.0785 MPa at a temperature of 25° C. by constant pressure dead-end filtration.

As the feed solution of bovine immunoglobulin, a solution prepared by diluting a bovine immunoglobulin solution (manufactured by Life Technology) with 0.15N NaCl to a concentration of 3 wt % and removing contaminants by prefiltration using PLANOVA 35N (manufactured by Asahi Kasei Corporation, formerly Asahi Chemical Industry Co., Ltd.) was used. The molecular weight distribution of bovine immunoglobulin in the unfiltered solution was measured by liquid chromatography. As a result, the monomer content was 80% or more.

This feed solution was filtered for three hours using a separation membrane to obtain the filtrate.

The bovine immunoglobulin concentration in the feed solution and in the filtrate was calculated by measuring the absorbance at 280 nm using a UV spectrophotometer.

In the case of separating small particles such as physiologically active products and large particles such as viruses by using a virus removal membrane based on the sieving principle, pores with a pore size intermediate between the diameters of these two types of particles are substantially effective. In order to allow the pores having a diameter in such a range to exhibit sufficient effectiveness, it is inevitable for the pore structure of the membrane to have a region with a certain degree of homogeneity. Specifically, in the pore structure of the membrane of the present invention, the thickness of the region in which the pore size logarithmic standard deviation $\sigma_g$ is 2.0 or less is preferably 3–90 μm, and still more preferably 15–50 μm. Said homogeneity may be directly measured by pore size measurement using an electron microscope.

The membrane of the present invention having the above pore structure wherein exhibits a higher log reduction value for porcine parvovirus not only in the initial stage of filtration but also subsequent filtration, and simultaneously allows bovine immunoglobulin to pass therethrough at a higher rate, because of the increased capacity of the region with a certain degree of homogeneity.

The greater the thickness of the region in which the pore size logarithmic standard deviation $\sigma_g$ is 2.0 or less, the higher the log reduction value for porcine parvovirus. However, an excessive increase in the thickness gives rise to a disadvantage with respect to permeability for bovine immunoglobulin.

The pore size logarithmic standard deviation $\sigma_g$ is calculated according to the following equation.

$$ln\sigma_g = ((\Sigma \Delta n_i (lnD_{pi} - lnD_{pg})^2 / N)^{1/2}$$

$$lnD_{pg} = \Sigma \Delta n_i lnD_{pi}/N$$

$\Delta n_i$: Number of pores with a pore size of $D_{pi}$ $D_{pi}$: Pore size (nm)

$D_{pg}$: Logarithmic average pore size (nm)

N: Total number of pores

The pore size of the membrane is measured through an electron microscope. The membrane is embedded in a polymer resin such as an acrylic resin. The embedded membrane is cut into a thin piece using a conventional method so that the lateral cross section of the membrane is exposed. The cut cross section of the membrane is photographed using a scanning electron microscope (SEM). The obtained photograph is analyzed by image processing. The cross section of the membrane is divided in the direction of the thickness. The pore size ($D_{pi}$) and the number of pores ($\Delta n_i$) are determined for each divided region. The pore size referred herein means the diameter converted the pore shown in the SEM photograph into a real circle.

In the present invention, the suitable purified water permeation rate is preferably 70–200 l/h/0.1 MPa, and still more preferably 90–120 l/h/0.1 MPa per m² of the membrane area. Allowing the purified water permeation rate to which all the pores in the membrane contribute to be 70 l/h/0.1 MPa or more per m² of the membrane area enables the amount of filtration and permeability for solution of physiologically active products to be increased to a practical level. This is particularly advantageous in the increase in the volume of filtration of the solution of physiologically active products. If the purified water permeation rate to which all the pores in the membrane contribute exceeds 200 l/h/0.1 MPa per m² of the membrane area, it is difficult to increase the log reduction value for porcine parvovirus to 3 or more at both 0–5 l/m² filtration and 50–55 l/m² filtration.

The purified water permeation rate referred herein means the value shown as the flow rate of purified water filtered under a trans-membrane differential pressure of 0.1 MPa at a temperature of 37° C. in the unit of l/h/0.1 MPa per m² of the membrane area (in a dry state). Purified water referred herein means water purified by ultrafiltration.

The skin layer referred in the present invention means an extremely thin layer present on one side or both sides of the membrane, which has a fine structure in comparison with the inside of the membrane. Generally, a membrane of which filtration characteristics are owed to only the skin layer may also achieve a purified water permeation rate of 70 l/h/0.1 MPa per m² of the membrane area or more. However, such a membrane hardly achieve ≧3 LRV for porcine parvovirus at both 0–5 l/m² filtration and 50–55 l/m² filtration. This is because the skin layer inevitably has defects such as pinholes or cracks, thereby resulting in unreliability relating to the virus reduction value.

The suitable thickness of the membrane of the present invention is 5–100 μm, and preferably 20–100 μm. In the production of the membrane of the present invention, the coagulation rate inside the membrane greatly varies depending on the distance from the surface of the membrane. Therefore, if the thickness of the membrane exceeds 100 μm, it is difficult to control the pore structure of the membrane. Therefore, the thickness of the membrane is preferably 100 μm or less. The membrane have need of a certain degree of thickness in order to ensure ≧3 LRV for porcine parvovirus at both 0–5 l/m² filtration and 50–55 l/m² filtration. Therefore, the thickness of the membrane is preferably 5 μm or more.

The membrane referred in the present invention is a virus removal membrane for removing viruses, an ultrafilter membrane, microfiltration membrane, or the like. As the material for the membrane, regenerated cellulose, polyvinylidene fluoride, polysulfone, polyacrylonitrile, and the like can be given, but the materials other than those materials may be included. The form of the membrane may be any of a hollow fiber membrane, flat membrane, pleat membrane, and spiral membrane. In addition, the membrane may be a composite membrane in which membranes are layered.

The physiologically active products referred in the present invention means physiologically active products generally used in the fields of medicine, medication, and diagnosis reagents. Specific examples include proteins, polypeptides, polysaccharides, combinations thereof, and the like. The origin of these physiologically active products is human, animal, or cultured cells. These physiologically active products include physiologically active products produced by cultured animal cells using genetic recombination or cell fusion technique, physiologically active products produced by secretory tissues of animals using a transgenic technique, and the like.

As examples of proteins, blood coagulation factors such as F-IX, F-XI, F-VIII, F-VII, fibrinogen, thrombin, antithrombin-III, and mixtures thereof, human immunoglobulin such as IgG, IgA, IgD, IgE, and IgM, alubumin, α-1 protease inhibitor, trypsin inhibitor, protease inhibitor, streptokinase, apolipoprotein, and growth factors, and the like can be given. As examples of polypeptides, physiologically active polypeptides such as recombinant human growth hormone produced using mammal cells, protease inhibitor originating from bovine tissue, and the like can be given. As examples of polysaccharides, glycosaminoglycans such as heparin, heparin fragments, heparin derivatives, heparan sulfate, and hyaluronic acid can be given.

Human immunoglobulin products generally exhibit low permeability during membrane filtration due to the high concentration in the solution. Therefore, it is difficult to remove human parvovirus B19, poliovirus, or the like while allowing human immunoglobulin products to pass through the membrane. However, the membrane of the present invention can be suitably used for human immunoglobulin products due to high permeability and the high reduction value of human parvovirus B19, poliovirus, or the like. Therefore, the present invention exhibits especially significant effect in the case where the physiologically active products are human immunoglobulin.

The solution of physiologically active products is preferably filtered under conditions in which clogging is hard to occur taking permeability into consideration. It is also practically preferable from the viewpoint of economy.

There are no specific limitations to the protein concentration in the case of using human immunoglobulin. The protein concentration is preferably 5 wt % or less, and still more preferably 3 wt % or less for practical use.

As a method for producing the membrane of the present invention using various types of polymers, non-solvent induced phase separation or thermally induced phase separation is generally used. The objective membrane structure can be produced by adjusting the raw material polymer concentration in the polymer solution and equilibrium factors and kinetics factors in chemical changes during phase separation and coagulation.

More specifically, in the case of producing a hollow fiber membrane using a double spinning nozzle, the membrane structure varies depending on chemical equilibrium factors and kinetic factors during membrane production such as the polymer concentration in the spinning solution, inner solution composition, outer solution composition, extruding rate of the spinning solution, and winding rate of the membrane. If the extruding rate and the winding rate are low, the pore size distribution become narrow and the thickness of the effective region of the membrane having a homogeneous pore size is increased. However, an excessive lowering in the extruding rate and the winding rate results in a decrease in production efficiency, and is not practical. Therefore, in the case of setting the extruding rate and the winding rate to practical constant values, the membrane structure can be changed by adjusting the polymer concentration in the spinning solution, inner solution composition, and outer solution composition. If the non-solvent concentration in the inner solution and the outer solution is decreased, the pore size distribution of the region inside the membrane which substantially contributes separation can be made narrower and the thickness of this region can be increased. Therefore, the BP/γ ratio and the log reduction value for porcine parvovirus tend to be increased.

The method for producing the filter membrane of the present invention is described below in detail taking a hollow fiber membrane formed of cuprammonium regenerated cellulose as an example. A cuprammonium cellulose solution and an aqueous solution including a non-solvent which causes micro-phase separation (hereinafter called "coagulating solution") are prepared using a conventional method (Japanese Patent Applications Laid-open No. 59-204912 and No. 59-204911, for example). Specifically, cellulose is dissolved as the raw material of the membrane in a cuprammonium solution to prepare a cuprammonium cellulose solution with a cellulose concentration of about 7.0–8.0 wt %. The coagulating solution comprises two kinds of solutions of an outer solution which is allowed to act from outside the hollow fiber and an inner solution which is introduced into the hollow fiber and allowed to act therefrom. The composition of the outer solution preferably has an acetone concentration of about 20–35 wt % and an ammonia concentration of about 0–0.1 wt %. The composition of the inner solution preferably has an acetone concentration of about 30–50 wt % and an ammonia concentration of about 0–0.5 wt %. This example illustrates a non-solvent induced membrane production method using acetone as the non-solvent. It is preferable to decrease the concentration of the non-solvent which causes micro-phase separation in the coagulating solution. This is because the pore size distribution in the region inside the membrane can be made narrower, and the thickness of this region can be further increased by decreasing the non-solvent concentration.

The cuprammonium cellulose solution and the coagulating solution prepared as described above are subjected to spinning, coagulation, regeneration, washing with water, and drying under vacuum using a method disclosed in Japanese Patent Application Laid-open No. 4-371221 to obtain a hollow fiber membrane.

BEST MODE FOR CARRYING OUT THE INVENTION

The present invention is described below by examples, which should not be construed as limiting the present invention.

EXAMPLES 1–3

A cuprammonium cellulose solution and a coagulating solution were prepared using a method disclosed in Japanese Patent Application Laid-open No. 59-204912. A hollow fiber membrane was produced using a method disclosed in Japanese Patent Application Laid-open No. 4-371221. Specifically, cotton linters (average molecular weight: 1.44×$10^5$) were dissolved in a cuprammonium solution prepared using a conventional method to prepare a spinning solution with a cellulose concentration of 7.5 wt %. The spinning solution was extruded from an outer nozzle of a circular double spinneret. At the same time, an inner solution having a composition shown in Table 1 was extruded from a center nozzle of the double spinning nozzle. The extruding rate of the spinning solution is shown in Table 1. The solutions were extruded into an outer solution having a composition shown in Table 1 and winded. The winding rate was 10 m/minute.

The pore structure of the membrane can be controlled by adjusting the cellulose concentration, outer solution composition, and inner solution composition, whereby the membrane of the present invention can be obtained.

A U-shaped narrow tube disclosed in Japanese Patent Application Laid-open No. 4-371221 was used as a coagulation bath in this coagulation step. The winded hollow fiber membrane was subjected to regeneration with dilute sulfuric acid solution, washing with water, and drying under vacuum using a method disclosed in Japanese Patent Application Laid-open No. 4-371221. The hollow fiber membrane thus obtained was assembled into a filter by a conventional method using a polyurethane sealant.

The inner diameter, thickness, BP/γ ratio, purified water permeation rate, porcine parvovirus LRV, and bovine immunoglobulin permeability of the resulting hollow fiber membrane are shown in Table 1. The bubble point, purified water permeation rate, porcine parvovirus LRV, and bovine immunoglobulin permeability were measured according to the above-described methods. In the examples, the bubble point was measured by producing low pressure test conditions measurable within the range of withstand pressure of the membrane using perfluorocarbon with surface tension γ of 0.012 (N/m) as wetting liquid, and using nitrogen as a gas.

As a result of observation using an electron microscope, the membranes in Examples 1–3 had no skin layer on the surface.

TABLE 1

|  | Example | | |
|---|---|---|---|
|  | 1 | 2 | 3 |
| Cellulose concentration (wt %) | 7.5 | 7.5 | 7.5 |
| Outer solution composition | | | |
| Acetone concentration (wt %) | 30 | 25 | 30 |
| Ammonia concentration (wt %) | 0 | 0 | 0 |
| Inner solution composition | | | |
| Acetone concentration (wt %) | 40 | 45 | 40 |
| Ammonia concentration (wt %) | 0 | 0.65 | 0 |
| Extruding rate of spinning solution (ml/min) | 3.65 | 3.65 | 3.00 |
| Inner diameter (μm) | 404 | 414 | 396 |
| Membrane thickness (μm) | 32 | 30 | 25 |
| BP/γ ratio (MPa/(N/m)) | 120 | 135 | 115 |
| Purified water permeation rate[*1] | 107 | 97 | 118 |
| Porcine parvovirus LRV[*2] | 5.1 | >6.0 | 4.1 |
| Porcine parvovirus LRV[*3] | 4.2 | >6.0 | 3.1 |
| Bovine immunoglobulin permeability (%) | >90 | >6.0 | >90 |

[*1] l/h/0.1 MPa per $m^2$ of membrane area
[*2] Volume of virus solution filtered: 0–5 (l/$m^2$)
[*3] Volume of virus solution filtered: 50–55 (l/$m^2$)

The porosity measured in the direction of the thickness and the logarithmic standard deviation $\sigma_g$ of the pore size distribution of the membrane in Example 1 are shown in Table 2. In the membrane in Example 1, the thickness of a region with a logarithmic standard deviation $\sigma_g$ of 2.0 or less was 20 μm (corresponding to 63% of thickness of membrane).

TABLE 2

| Region in thickness direction (%) | Porosity (%) | Logarithmic standard deviation |
|---|---|---|
| 0–12 | 51 | 2.48 |
| 12–25 | 29 | 2.08 |
| 25–37 | 20 | 1.82 |
| 37–49 | 27 | 1.88 |
| 49–62 | 27 | 1.86 |
| 62–75 | 26 | 1.79 |
| 75–88 | 20 | 1.82 |
| 88–100 | 35 | 2.12 |

From the relation between human parvovirus B19 and porcine parvovirus, the membranes in Examples 1–3 can be estimated to exhibit virus removal performance for human parvovirus B19 equal to that for porcine parvovirus. From the relation between bovine immunoglobulin and human immunoglobulin, high permeability relating to bovine immunoglobulin obtained in Examples 1–3 is easily estimated to be achieved even in the practical process for producing human immunoglobulin preparations at the same or higher level.

Specifically, the membranes in Examples 1–3 allow physiologically active products to pass therethrough at a practical level and are capable of removing small viruses such as human parvovirus B19 or poliovirus from solutions of medicinal products or physiologically active products used as the raw materials of medicinal products which have risk of the contamination with viruses, therefore these are excellent membranes capable of providing safer products.

COMPARATIVE EXAMPLES 1–3

Hollow fiber membranes of Comparative Examples 1–3 were prepared in the same manner as in Examples 1–3. The compositions of the cuprammonium cellulose solution and the coagulating solution (inner and outer solutions) were as shown in Table 3.

The inner diameter, thickness, BP/γ ratio, purified water permeation rate, porcine parvovirus LRV, and bovine immunoglobulin permeability of the resulting hollow fiber membrane are shown in Table 3.

The bubble point, purified water permeation rate, porcine parvovirus LRV, and bovine immunoglobulin permeability were measured according to the above-described methods. In the comparative examples, the bubble point was measured by producing low pressure test conditions measurable within the range of withstand pressure of the membrane using perfluorocarbon having a surface tension γ of 0.012 (N/m) as wetting liquid, and using nitrogen as a gas in the same manner as described in the above examples.

As is clear from the results shown in Table 3, the membranes in Comparative Examples 1 and 3 are estimated to have high human immunoglobulin permeability, but have little capability for removing small viruses such as human parvovirus B19. The membrane in Comparative Example 2 is estimated to be able to highly remove small viruses such as human parvovirus B19, but have no human immunoglobulin permeability at a practical level.

TABLE 3

| | Comparative Example | | |
|---|---|---|---|
| | 1 | 2 | 3 |
| Cellulose concentration (wt %) | 6.96 | 7.5 | 7.5 |
| Outer solution composition | | | |
| Acetone concentration (wt %) | 37.5 | 37.5 | 30 |
| Ammonia concentration (wt %) | 0.1 | 0.1 | 0 |
| Inner solution composition | | | |
| Acetone concentration (wt %) | 53 | 45 | 53 |
| Ammonia concentration (wt %) | 0.65 | 0.65 | 0.65 |
| Extruding rate of spinning solution (ml/min) | 3.65 | 3.00 | 3.65 |
| Inner diameter (μm) | 330 | 330 | 345 |
| Membrane thickness (μm) | 35 | 26 | 34 |
| BP/γ ratio (MPa/(N/m)) | 69.6 | 137 | 105 |
| Purified water permeation rate*[1] | 308 | 59 | 122 |
| Porcine parvovirus LRV*[2] | 0.2 | >4.9 | 2.1 |
| Porcine parvovirus LRV*[3] | 0.1 | >5.1 | 2.1 |
| Bovine immunoglobulin permeability (%) | 100 | 55 | >95 |

*[1] l/h/0.1 MPa per $m^2$ of membrane area
*[2] Volume of virus solution filtered: 0–5 (l/$m^2$)
*[3] Volume of virus solution filtered: 50–55 (l/$m^2$)

INDUSTRIAL APPLICABILITY

According to the membrane of the present invention, in the filtration of solutions of medicinal products or physiologically active products used as raw materials of medicinal products which may be contaminated by viruses, the membrane can achieve superior performance for removing small viruses such as human parvovirus B19 or poliovirus (durability of $\geq 3$ LRV for human parvovirus B19, for example) and high permeation performance for physiologically active products (human immunoglobulin permeability of 70% or more, for example), thereby the present invention can also provide technologies for preparing safer preparations.

What is claimed is:

1. A filter membrane for solutions of physiologically active products, comprising a filter membrane having a ratio (BP/γ) of a bubble point BP (MPa) to surface tension γ (N/m) of 110 or more and a permeability for bovine immunoglobulin with a monomer content of 80% or more of 70% or more.

2. A filter membrane for solutions of physiologically active products, comprising a filter membrane having a log reduction value for porcine parvovirus of 3 or more at both a 0–5 l/$m^2$ filtration volume and a 50–55 l/$m^2$ filtration volume, and a permeability for bovine immunoglobulin with a monomer content of 80% or more of 70% or more.

3. A filter membrane for solutions of physiologically active products, comprising a filter membrane having a ratio (BP/γ) of a bubble point BP (MPa) to surface tension γ (N/m) of 110 or more, a log reduction value for procine parvovirus of 3 or more at both a 0–5 l/$m^2$ filtration volume and a 50–55 l/$m^2$ filtration volume, and a permeability for bovine immunoglobulin with a monomer content of 80% or more of 70% or more.

4. The filter membrane according to any one of claims 1 to 3, wherein, in a pore structure of the filter membrane, the thickness of a region in which a pore size logarithmic standard deviation $\sigma_g$ is 2.0 or less is 3–90 μm.

5. The filter membrane according to any one of claims 1 to 3, wherein the filter membrane further has a purified water permeation rate of 70–200 l/h/0.1 MPa per m² of membrane area.

6. The filter membrane according to any one of claims 1 to 3, wherein the filter membrane has no skin layer on a surface thereof.

7. The filter membrane according to any one of claims 1 to 3, wherein the filter membrane has a thickness of 5–100 μm.

* * * * *